United States Patent
Seong et al.

(10) Patent No.: US 10,821,127 B2
(45) Date of Patent: Nov. 3, 2020

(54) COMPOSITION FOR INHIBITING MYELOID-DERIVED SUPPRESSOR CELLS COMPRISING DECITABINE OR ITS PHARMACEUTICALLY ACCEPTABLE SALT AS ACTIVE INGREDIENT

(71) Applicant: SNU R&DB Foundation, Seoul (KR)

(72) Inventors: Seung-Yong Seong, Seoul (KR); Jung Ah Cho, Seoul (KR); Tae Joo Kim, Seoul (KR); Hyeon Park, Gangwon-do (KR)

(73) Assignee: SHAPERON INC., Seoul (KR)

( * ) Notice: Subject to any disclaimer, the term of this patent is extended or adjusted under 35 U.S.C. 154(b) by 0 days.

(21) Appl. No.: 15/347,216

(22) Filed: Nov. 9, 2016

(65) Prior Publication Data
US 2017/0128477 A1    May 11, 2017

Related U.S. Application Data

(60) Provisional application No. 62/252,850, filed on Nov. 9, 2015.

(51) Int. Cl.
*A61K 31/706*  (2006.01)
*A61K 45/06*  (2006.01)

(52) U.S. Cl.
CPC ............ *A61K 31/706* (2013.01); *A61K 45/06* (2013.01)

(58) Field of Classification Search
CPC .............................. A61K 31/706; A61K 45/06
See application file for complete search history.

(56) References Cited

U.S. PATENT DOCUMENTS

| | | | | |
|---|---|---|---|---|
| 6,613,753 B2 * | 9/2003 | Rubinfeld | ............... | A61K 31/00 514/49 |
| 8,242,248 B2 * | 8/2012 | Soper | ................. | G01N 33/5011 530/387.1 |

FOREIGN PATENT DOCUMENTS

| WO | 2002067681 | * | 9/2002 |
| WO | 2011/116299 A1 | | 9/2011 |
| WO | 2013/082591 A1 | | 6/2013 |

OTHER PUBLICATIONS

Daurkin et al., Generation of antigen-presenting cells from tumor infiltrated CD11b myeloid cells with DNA demethylating agent 5-aza-2'-deoxycytidine; Cancer Immunology, Immunotherapy:CII, (May 2010) vol. 59,No. 5, pp. 697-706.*
Suzanne Ostrand-Rosenberg et al., Myeloid-Derived Suppressor Cell:Linking Inflammation and Cancer; J. Immunology 2009; 182: 4499-4506.*
The Nature of Myeloid-Derived Suppressor Cells in the Tumor Microenvironment Vinit Kumar,1,2 Sima Patel,1,2 Evgenii Tcyganov,1,2.*
Circulating and Tumor-Infiltrating Myeloid-Derived Suppressor Cells in Patients with Colorectal Carcinoma Bin Zhang1., Zhijun Wang2., Liangliang Wu3, Meng Zhang1, Wei Li4, Jianhua Ding1, Jun Zhu1, Huafeng Wei5*, Ke Zhao1.*
Garrido-Laguna, KA McGregor et al., A phase I/II Study of decitabine in combination with Panitumumab in patients with wild-type (wt) KRAS metastatic colorectal cancer; Investigational New Drugs, 31 1257-1264 (2013).*
Dmitry I. Gabrilovich et al. "Myeloid-derived suppressor cells as regulators of the immune system". Nature Reviews Immunology, vol. 9, pp. 162-174 (Mar. 2009).
Eiji Suzuki et al. "Gemcitabine Selectively Eliminates Splenic Gr-1+/CD11b+ Myeloid Suppressor Cells inTumor-Bearing Animals and Enhances Antitumor ImmuneActivity". Clin Cancer Res 2005; 11(18), pp. 6713-6721 (Sep. 15, 2005).
Je-In Youn et al., Subsets of Myeloid-Derived Suppressor Cells in Tumor Bearing Mice, J Immunol, Oct. 15, 2008, pp. 5791-5802.

* cited by examiner

*Primary Examiner* — Mark L Shibuya
*Assistant Examiner* — Ebenezer O Sackey
(74) *Attorney, Agent, or Firm* — Novick, Kim & Lee, PLLC; Jae Youn Kim

(57) ABSTRACT

The present invention relates to a method for inhibiting myeloid-derived suppressor cells or treating cancer comprising administering a pharmaceutical composition containing decitabine or its pharmaceutically acceptable salt as an active ingredient. The decitabine suppresses creation of a cell population of myeloid-derived suppressor cells (MDSC) created in spleen and bone marrow in tumorigenic mice and induces apoptosis of the MDSC cell population. Therefore, the decitabine may be useful as agents for treating MDSC-related diseases and anticancer immunotherapy, or an anticancer supplement.

6 Claims, 15 Drawing Sheets

Specification includes a Sequence Listing.

SEQUENCE LISTING

```
<160> NUMBER OF SEQ ID NOS: 6

<210> SEQ ID NO 1
<211> LENGTH: 25
<212> TYPE: DNA
<213> ORGANISM: Artificial Sequence
<220> FEATURE:
<223> OTHER INFORMATION: IL6 primer forward

<400> SEQUENCE: 1
tggagtcaca gaaggagtgg ctaag                                           25

<210> SEQ ID NO 2
<211> LENGTH: 25
<212> TYPE: DNA
<213> ORGANISM: Artificial Sequence
<220> FEATURE:
<223> OTHER INFORMATION: IL6 primer reverse

<400> SEQUENCE: 2
tctgaccaca gtgaggaatg tccac                                           25

<210> SEQ ID NO 3
<211> LENGTH: 22
<212> TYPE: DNA
<213> ORGANISM: Artificial Sequence
<220> FEATURE:
<223> OTHER INFORMATION: IFN gamma primer forward

<400> SEQUENCE: 3
aggtcaacaa cccacaggtc ca                                              22

<210> SEQ ID NO 4
<211> LENGTH: 22
<212> TYPE: DNA
<213> ORGANISM: Artificial Sequence
<220> FEATURE:
<223> OTHER INFORMATION: IFN gamma primer reverse

<400> SEQUENCE: 4
ccagatacaa ccccgcaatc ac                                              22

<210> SEQ ID NO 5
<211> LENGTH: 20
<212> TYPE: DNA
<213> ORGANISM: Artificial Sequence
<220> FEATURE:
<223> OTHER INFORMATION: VEGF primer forward

<400> SEQUENCE: 5
ctgtgcaggc tgctgtaacg                                                 20
```

```
<210> SEQ ID NO 6
<211> LENGTH: 20
<212> TYPE: DNA
<213> ORGANISM: Artificial Sequence
<220> FEATURE:
<223> OTHER INFORMATION: VEGF primer reverse

<400> SEQUENCE: 6
gttcccgaaa ccctgaggag                                               20
```

COMPOSITION FOR INHIBITING MYELOID-DERIVED SUPPRESSOR CELLS COMPRISING DECITABINE OR ITS PHARMACEUTICALLY ACCEPTABLE SALT AS ACTIVE INGREDIENT

CROSS-REFERENCE TO RELATED APPLICATION

This application claims priority to and the benefit of U.S. provisional application No. 62/252,850, filed on Nov. 9, 2015, which is incorporated herein by reference in its entirety.

BACKGROUND OF THE INVENTION

Field of the Invention

The present invention relates to a method for inhibiting myeloid-derived suppressor cells or treating cancer comprising administering a pharmaceutical composition containing decitabine or its pharmaceutically acceptable salt as an active ingredient.

Description of the Related Art

Efforts to develop an immune therapy for tumors by applying interaction between cancer cells and immune cells have been continued. Recently, unlike a classic host defense mechanism among various immune cells, it was found that cells with the nature of actively supplementing and promoting the growth of the tumor exist and fields of developing therapies of suppressing the growth of the cancer cells through these regulations have been actively researched.

Myeloid cells are originated from a hematopoietic stem cell. The myeloid cells mainly exist in bone marrow and lymphatic tissues as a lot of hematopoietic stem cells which exist in the body. Finally, the myeloid cells are differentiated into macrophages, dendritic cells, and granulocytes, but these cells do not have a specific hierarchical structure and have a feature that the myeloid cells having differentiation having various steps are variously distributed specifically to tissues and environments. The cells exist in a microenvironment of the tumor and any role in the generation and the growth of the tumor has been known for a long time, but particularly, it is known in recent years that the cells serve to promote tumor angiogenesis and assisting invasion and metastasis of the tumor cells.

Myeloid-derived suppressor cells (MDSC) are cells having immunosuppressive action among myeloid cells and as a cell population including very widely undifferentiated myeloid cells, are increased in a generation state of tumors or inflammation. It is known that these MDSC have the immunosuppressive action through a direct contact between most of cells and it is understood that the immunosuppressive function is performed by secreting materials such as cytokines having a short half-life. As currently known agonists, arginase I, inducible nitric oxide synthesis (iNOS), reactive oxygen species (ROS), nitrogen monoxide, and the like are included. The arginase I and the iNOS directly suppress the proliferation of the T-cells as representative T-cell inhibitors and the ROS and the nitrogen monoxide suppress antigen recognition capability through a post-translational modification process of a T-cell receptor (Nat Rev Immunol 2009; 9(3): 162-74). Based on researches of functions and action mechanisms of these MDSC, recently, efforts to develop new cancer therapies through these regulations have been accelerated.

In a preclinical model, a chemotherapeutic agent which is known to directly reduce the MDSC is just gemcitabine and 5-fluorouracil (5-FU). It is reported that the gemcitabine significantly reduces the number of MDSC in the spleen in tumor-induced mice (Clin Cancer Res 2005; 11: 6713-6721). It is known that the 5-FU also significantly reduces the MDSC, and it is reported that the reduction degree thereof is larger than that of the gemcitabine.

As another method for suppressing the MDSC, in International Patent Publication No. 2013-082591, a method of adding miR-142 and/or miR-223 ribonucleotides to the MDSC is disclosed. That is, it is disclosed that the number of miR-142 and/or miR-223 ribonucleotides may be reduced so that the MDSC is differentiated into macrophages, dendritic cells, and the like.

As yet another method for suppressing the MDSC, in International Patent Publication No. 2011-116299, a method of using bisphosphonate or a CCR2 inhibitor as an adjuvant is disclosed.

The methods of suppressing the MDSC indicate a possibility that the anticancer immunotherapy achieves a clinical effect, but do not yet achieve the treatment results to reduce a significant change in survival rate of the patient. Particularly, a drug such as the gemcitabine in the related art simultaneously reduces the MDSC and the CD3 T cells and thus immunocompetence of cancer patients is seriously deteriorated to have a negative effect on the prognosis of the cancer patients. Accordingly, in the cancer patients, a drug of selectively removing only the MDSC without removing CD3 T lymphocytes is required. Further, in the cancer patients, at the time of primarily removing the MDSC and additionally treating secondary immunity, when the number of T lymphocytes in the body of the patient is decreased, the effect of the immunotherapy is very low and thus the retention of the T lymphocytes is absolutely required when removing the MDSC by the drug. Accordingly, development of drugs capable of replacing the existing gemcitabine of removing up to the T lymphocytes in addition to the removal of the MDSC is required.

Therefore, the inventor of the present invention made an effort for developing drugs which can replace anticancer immunotherapeutic agents in the related art and are applicable to the clinical as an adjunctive therapy in the anticancer immunotherapy and as a result, verified that decitabine as a chemotherapeutic agent having a specific effect to the bone marrow suppresses the generation of MDSC cell populations generated in the spleen and the bone marrow of the tumorigenic mice and induces apoptosis of the MDSC cell populations. As a result, the inventors found that the decitabine can be used for treating MDSC-related diseases or anticancer immunotherapy and completed the present invention.

SUMMARY OF THE INVENTION

An object of the present invention is to provide a method for inhibiting myeloid-derived suppressor cells, comprising administering to a subject an effective amount of a pharmaceutical composition containing decitabine or its pharmaceutically acceptable salt.

Another object of the present invention is to provide a method for treating cancer, comprising administering to a subject a pharmaceutical composition containing decitabine or its pharmaceutically acceptable salt; and an anticancer agent.

Yet another object of the present invention is to provide an anti-cancer supplement comprising decitabine or its pharmaceutically acceptable salt as an active ingredient.

An aspect of the present invention provides a method for inhibiting myeloid-derived suppressor cells, comprising administering to a subject an effective amount of a pharmaceutical composition containing decitabine or its pharmaceutically acceptable salt.

Another aspect of the present invention provides a method for treating cancer, comprising administering to a subject a pharmaceutical composition containing decitabine or its pharmaceutically acceptable salt; and an anticancer agent.

Yet another aspect of the present invention provides an anti-cancer supplement comprising decitabine or its pharmaceutically acceptable salt as an active ingredient.

According to the present invention, the decitabine suppresses creation of a cell population of myeloid-derived suppressor cells (MDSC) created in spleen and bone marrow in tumorigenic mice and induces apoptosis of the MDSC cell population to activate an immune response inhibited by the MDSC and prevent inhibition of the immune response of cancer vaccine in the related art, and thus the decitabine may be useful as agents for treating MDSC-related diseases and anticancer immunotherapy, or an anticancer supplement.

BRIEF DESCRIPTION OF THE DRAWING(S)

The application of the preferred embodiments of the present invention is best understood with reference to the accompanying drawings, wherein.

DETAILED DESCRIPTION OF THE PREFERRED EMBODIMENT(S)

Figure 1:
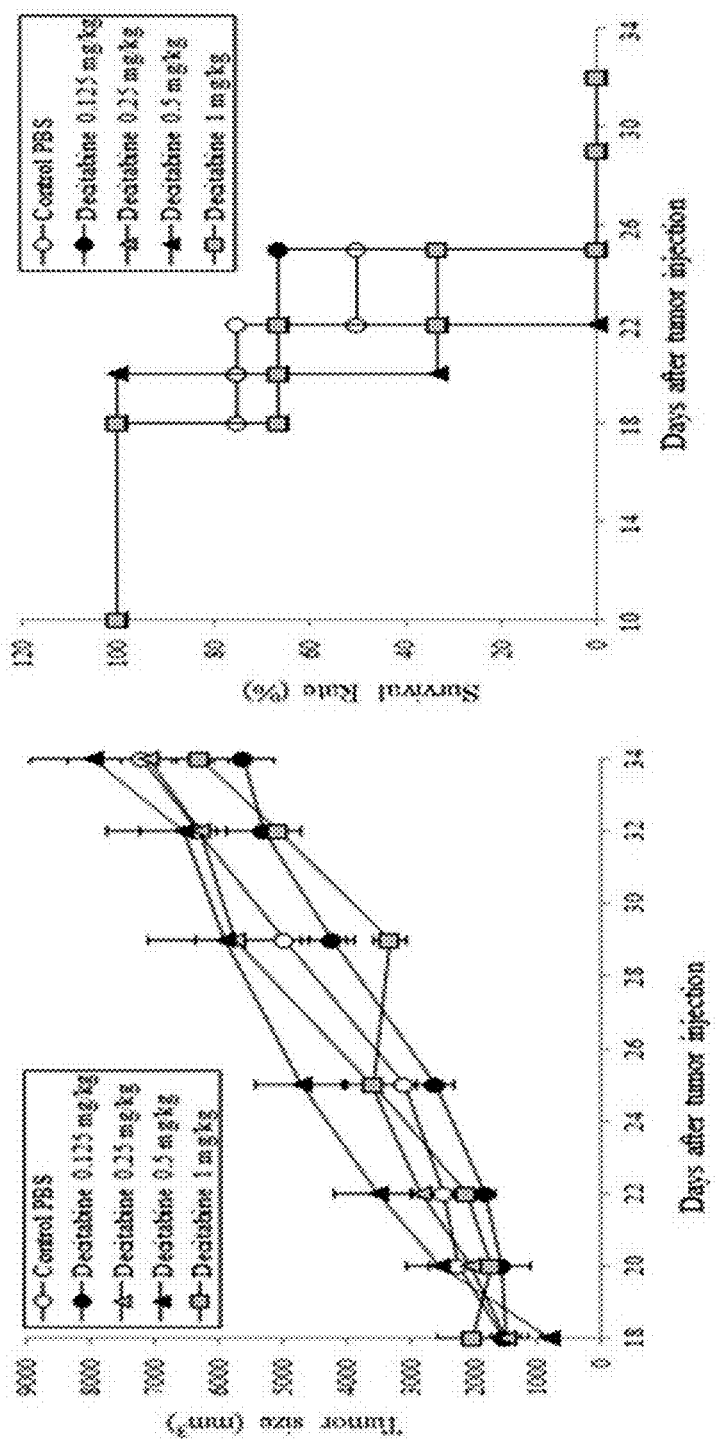
FIG. 1 is a diagram illustrating changes in tumor size and survival rate of mice according to administration of decitabine (DAC) for each concentration (0, 0.125, 0.25, 0.5, 1 mg/kg) in tumorigenic mice.

Hereinafter, the present disclosure will be described in detail.

The present invention provides a method for inhibiting myeloid-derived suppressor cells, comprising administering to a subject an effective amount of a pharmaceutical composition containing decitabine or its pharmaceutically acceptable salt.

The composition may be administered to the subject required to inhibit the myeloid-derived suppressor cells.

In the present invention, the "myeloid-derived suppressor cells" functions to suppress immunity by inhibiting activity of cytotoxic T lymphocyte. There is a positive function of suppressing unnecessarily excessive immune response such as autoimmune, but there is a negative function of generating or deteriorating diseases or interrupting proper treatment by suppressing immunity in a situation where immune response is required. For example, the myeloid-derived suppressor cells are largely increased in tumor or cancer patients, and this significantly reduces effects of administrating cancer vaccine to inactivate the efficacy of cancer vaccine. In such a situation, when the number of myeloid-derived suppressor cells is effectively reduced, the cancer treatment may be smoothly and effectively performed.

In the present invention, the "inhibiting of the myeloid-derived suppressor cells" includes up to suppressing activity of the myeloid-derived suppressor cells as well as reducing the number of myeloid-derived suppressor cells. The reducing of the number includes killing pre-generated cells or differentiating the cells to other cells as well as suppressing generation of the cells. In addition, all mechanisms referred to as "inhibition" from the biological point of view are included.

The myeloid-derived suppressor cells may be myeloid-derived suppressor cells of the subject having tumor, but are not limited thereto.

The myeloid-derived suppressor cells of the subject having the tumor may be at least one selected from the group consisting of phenotypes of CD11b$^+$Gr1$^{hi}$, CD11b$^+$F480$^-$Gr1$^+$, CD11b$^+$Ly6c$^{hi}$, CD11b$^+$Ly6c$^+$Ly6g$^+$, CD11b$^+$Ly6c$^{++}$Ly6g$^-$, CD11b$^+$Ly6c$^{++}$Ly6g$^-$, CD11b$^+$Lineage$^-$(CD3, CD14, CD19 and CD56)HLA-DR$^-$CD33$^+$ and CD11b$^+$CD14$^+$HLA-DR$^-$CD15$^-$, more preferably phenotypes of CD11b$^+$Gr1$^{hi}$, CD11b$^+$F480$^-$Gr1$^+$, CD11b$^+$Ly6c$^{hi}$, CD11b$^+$Ly6c$^+$Ly6g$^+$ and CD11b$^+$Ly6c$^{++}$Ly6g$^-$ in mice, and CD11b$^+$Ly6c$^{++}$Ly6g$^-$, CD11b$^+$Lineage$^-$(CD3, CD14, CD19 and CD56)HLA-DR$^-$CD33$^+$ and CD11b+CD14$^+$HLA-DR$^-$CD15$^-$ in human but are not limited thereto.

The tumor may be any one selected from the group consisting of liver cancer, stomach cancer, colon cancer, breast cancer, lung cancer, non-small cell lung cancer, bone cancer, pancreatic cancer, skin cancer, head or neck cancer, cutaneous or intraocular melanoma, uterine cancer, ovarian cancer, colorectal cancer, small intestine cancer, rectal cancer, anal cancer, fallopian tube cancer, endometrial cancer, cervical cancer, vaginal cancer, vulva cancer, Hodgkin's disease, esophageal cancer, small intestine cancer, lymph node cancer, bladder cancer, gallbladder cancer, endocrine cancer, thyroid cancer, parathyroid cancer, adrenal cancer, soft tissue sarcoma, urethra cancer, penis cancer, prostate cancer, adenocarcinoma, chronic or acute leukemia, lymphocytic lymphoma, bladder cancer, kidney or ureter cancer, renal cell carcinoma, renal pelvic carcinoma, central nervous system tumor, primary CNS tumor, spinal cord tumor, brainstem glioma, and pituitary adenoma, but is not limited thereto.

The decitabine may use any one which is commercially available or produced by a known chemical synthesis method, and has Chemical Formula disclosed by the following Chemical Formula 1 as 5-aza-2'-deoxycytidine.

[Chemical Formula 1]

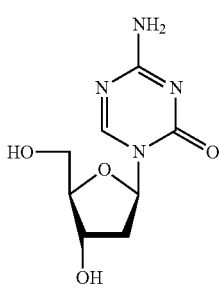

Further, the decitabine as a myelodysplastic syndromes (MDS) treating agent is a DNA methylation inhibitor having a treatment effect by suppressing DNA methylation and well-known as a material having three times larger treatment response rate than azacytidine as a treating agent which has been previously used.

The present invention includes all of its pharmaceutically acceptable salt and solvates, hydrates, racemates, or stereoisomers capable of being prepared therefrom as well as decitabine.

The decitabine of the present invention may be used in a form of its pharmaceutically acceptable salt and as the salt, acid additional salts formed by pharmaceutically acceptable free acid are useful. The acid additional salts are obtained from inorganic acids such as hydrochloric acid, nitric acid, phosphoric acid, sulfuric acid, hydrobromic acid, hydriodic acid, nitrous acid or phosphorous acid and non-toxic organic acids such as aliphatic mono and dicarboxylate, phenyl-substituted alkanoate, hydroxy alkanoate and alkandioate, aromatic acids, aliphatic and aromatic sulfonic acids. The pharmaceutically non-toxic salts include sulfate, pyrosulfate, bisulfate, sulfite, bisulfite, nitrate, phosphate, monohydrogen phosphate, dihydrogen phosphate, meta-phosphate, pyrophosphate chloride, bromide, iodide, fluoride, acetate, propionate, decanoate, caprylate, acrylate, formate, isobutyrate, caprate, heptanoate, propionic oleate, oxalate, malonate, succinate, suberate, sebacate, fumarate, maleate, butene-1,4-dioate, hexane-1,6-dioate, benzoate, chlorobenzoate, methylbenzoate, dinitro benzoate, hydroxybenzoate, methoxybenzoate, phthalate, terephthalate, benzene sulfonate, toluene sulfonate, chlorobenzene sulfonate, xylene sulfonate, phenylacetate, phenyl propionate, phenyl butyrate, citrate, lactate, hydroxybutyrate, glycollate, maleate, tartrate, methanesulfonate, propanesulfonate, naphthalene-1-sulfonate, naphthalene-2-sulfonate or mandelate.

The acid additional salt according to the present invention may be prepared by a general method, for example, dissolving the decitabine in a large amount of acid aqueous solution and precipitating the salt by using a water-miscible organic solvent, for example, methanol, ethanol, acetone, or acetonitrile. Further, a salt which is dried or precipitated by evaporating a solvent or a large amount of acid from the mixture may also be prepared through suction-filtering.

Further, a pharmaceutically acceptable metal salt may be prepared by using base. An alkali metal or alkaline earth metal salt is obtained by dissolving the compound in a large amount of alkali metal hydroxide or alkaline earth metal hydroxide solution and filtering an insoluble compound salt and then evaporating and drying a filtrate. In this case, the metal salt is pharmaceutically suitable to manufacture sodium, potassium or calcium salts. Further, the silver salt corresponding thereto is obtained by reacting alkali metal or alkaline earth metal salts with an appropriate silver salt (for example, silver nitrate).

The decitabine or its pharmaceutically acceptable salt may suppress expression of cytokines inducing generation of the myeloid-derived suppressor cells in a cancer site, and the cytokine may be at least one selected from the group consisting of IL-6, IFN-γ, and VEGF, but is not limited thereto.

In the preferred embodiment of the present invention, the inventors verified that in order to verify whether the decitabine suppresses the myeloid-derived suppressor cells produced from the bone marrow by the tumor, tumorigenic mice were prepared and the decitabine was administrated for each concentration, and as a result, an effect of suppressing the myeloid-derived suppressor cells by the decitabine is excellent in a dose range of 0.5 to 1 mg/kg.

Further, the inventors verified that the decitabine reduced production of cytokines inducing the creation of the myeloid-derived suppressor cells in the tumor, so that reduction in myeloid-derived suppressor cells by the tumor in addition to reduction in myeloid-derived suppressor cells in an immune organ by the decitabine was induced.

Accordingly, in the present invention, it is verified that the decitabine suppresses creation of a cell population of myeloid-derived suppressor cells created in spleen and bone marrow in tumorigenic mice and induces apoptosis of the cell population of myeloid-derived suppressor cells, and thus the decitabine may be used for treating myeloid-derived suppressor cells-related diseases.

When the composition according to the present invention is formulated, the formulation may be prepared by using diluents or excipients, such as a filler, an extender, a binding agent, a wetting agent, a disintegrating agent, and a surfactant, which are generally used.

In detail, a solid formulation for oral administration includes a tablet, a pill, a powder, a granule, a capsule, a troche agent, or the like, and the solid formulation may be prepared by mixing at least one excipient, for example, starch, calcium carbonate, sucrose or lactose, gelatin, or the like with at least one decitabine of the present invention. Further, lubricants such as magnesium stearate talc may be used in addition to simple excipients. A liquid formulation for oral administration may use a suspension, a solution, an emulsion, a syrup, and the like, and may include various excipients, for example, a wetting agent, a sweetener, an aromatic agent, a preserving agent, and the like in addition to water and liquid paraffin, as simple diluents which are commonly used.

A formulation for parenteral administration includes a sterile aqueous solution, a non-aqueous solution, a suspension, an emulsion, a lyophilizing agent, a suppository, and the like.

As the non-aqueous solution and the suspension, propylene glycol, polyethylene glycol, vegetable oils such as olive oil, injectable ester such as ethyl oleate, and the like may be used. As a matter of the suppository, witepsol, macrogol, tween 61, cacao butter, laurin, glycerol, gelatin, and the like may be used.

The composition according to the present invention is administrated with a pharmaceutically effective dose. In the present invention, the "pharmaceutically effective dose" means a amount which is sufficient to treat the diseases at a reasonable benefit/risk ratio applicable to medical treatment, and an effective dose level may be determined according to elements including a kind of disease of the patient, the severity, activity of a drug, sensitivity to a drug, a time of administration, a route of administration, and an emission rate, duration of treatment, and simultaneously used drugs and other elements well-known in the medical field. The composition of the present invention may be administrated as an individual treating agent or administrated in combination with other treating agents, sequentially or simultaneously administrated with treating agents in the related art, and administrated in single or multiple. It is important to administrate an amount capable of obtaining a maximum effect with a minimal amount without side effects by considering the elements and it may be easily determined by those skilled in the art.

Particularly, the effective dose of the composition according to the present invention may vary according to age, sex, and weight of the patient, and generally administrated by 0.1 mg to 100 mg per weight 1 kg, preferably administrated by 0.5 mg to 10 mg daily or every other day, or administrated one to three times per day. However, since the effective dose may be decreased or increased depending on the route of administration, the severity of obesity, sex, weight, age, and the like, the dose is not limited to the scope of the present invention in any way.

Further, the present invention provides a method for treating cancer, comprising administering to a subject a pharmaceutical composition containing decitabine or its pharmaceutically acceptable salt; and an anticancer agent.

The decitabine or its pharmaceutically acceptable salt have an anticancer supplement effect of significantly enhancing an effect of the anticancer agent by suppressing the myeloid-derived suppressor cells, for example, the myeloid-derived suppressor cells of which a phenotype is $CD11b^+Gr1^{hi}$, $CD11b^+F480^-Gr1^+$, $CD11b^+Ly6c^{hi}$, $CD11b^+Ly6c^+Ly6g^+$, $CD11b^+Ly6c^{++}Ly6g^-$, $CD11b^+Ly6c^{++}Ly6g^-$, $CD11b^+Lineage^-$(CD3, CD14, CD19 and CD56)$HLA-DR^-CD33^+$ or $CD11b^+CD14^+HLA-DR^-CD15^-$, more preferably phenotypes of $CD11b^+Gr1^{hi}$, $CD11b^+F480^-Gr1^+$, $CD11b^+Ly6c^{hi}$, $CD11b^+Ly6c^+Ly6g^+$ or $CD11b^+Ly6c^{++}Ly6g^-$ in mice, and $CD11b^+Ly6c^{++}Ly6g^-$, $CD11b^+Lineage^-$(CD3, CD14, CD19 and CD56)$HLA-DR^-CD33^+$ or $CD11b^+CD14^+HLA-DR^-CD15^-$ in human.

The anticancer agent may be at least one selected from the group consisting of a chemotherapeutic agent, a targeted therapeutic agent, an antibody therapeutic agent, an immunotherapeutic agent, and a hormone therapeutic agent, but is not limited thereto.

The chemotherapeutic agent includes, for example, metabolic antagonists (for example, folic acid, purine, and pyrimidine derivatives), alkylating agents (for example, nitrogen mustards, nitrosoureas, platinum, alkyl sulfonates, hydrazine, triazine, aziridine, spindle inhibitors, cytotoxic agents, topoisomerase inhibitors, and others), and low-methylating agents (for example, zebularine, isothiocyanate, azacytidine (5-azacytidine), 5-fluoro-2'-deoxycytidine, 5,6-dihydro-5-azacytidine and others), but is not limited thereto.

The targeted therapeutic agent includes a specific formulation to non-regulatory proteins of cancer cells, for example, tyrosine kinase inhibitors, such as axitinib, bosutinib, cediranib, dasatinib, erlotinib, imatinib, gefitinib, lapatinib, lestaurtinib, nilotinib, semaxanib, sorafenib, sunitinib, and vandetanib, and/or cyclin-dependent kinase inhibitors, such as alvocidib and seliciclib, but is not limited thereto.

The antibody therapeutic agent includes an antibody agent specifically bound to proteins on the surface of the cancer cells, for example, trastuzumab, rituximab, tositumomab, cetuximab, panitumumab, alemtuzumab, bevacizumab, edrecolomab, and gemtuzumab, but is not limited thereto.

The immunotherapeutic agent includes an agent designed to induce a self-immune system of a subject in order to attack the tumor, for example, ipilimumab, avelumab, nivolumab, and pembrolizumab, but is not limited thereto.

The hormone therapeutic agent includes an agent of suppressing a growth of the cancer by providing or interrupting a hormone in a specific cancer, for example, tamoxifen and diethylstilbestrol, but is not limited thereto.

The appropriate dose of the anticancer agent is widely known in the art and thus may be administrated by a known reference in the art according to a state of each patient. A particular dose is determined within a level of those skilled in the art, and a daily dose thereof is particularly 1 mg/kg/day to 10 mg/kg/day and more particularly 10 mg/kg/day to 100 mg/kg/day, but is not limited thereto and may vary according to various factors including age, health status, complications, and the like of a subject to be administrated.

In the exemplary embodiment of the present invention, it is verified that the decitabine suppresses creation of a cell population of myeloid-derived suppressor cells created in spleen and bone marrow in tumorigenic mice and induces apoptosis of the cell population of myeloid-derived suppressor cells, and thus the decitabine may be used for anticancer treatment.

Further, the present invention provides an anti-cancer supplement comprising decitabine or its pharmaceutically acceptable salt as an active ingredient.

The supplement may be administered in combination with an anticancer agent, and have an anticancer supplement effect of significantly enhancing an effect of the anticancer agent by suppressing the myeloid-derived suppressor cells, for example, the myeloid-derived suppressor cells of which a phenotype is $CD11b^+Gr1^{hi}$, $CD11b^+F480^-Gr1^+$, $CD11b^+Ly6c^{hi}$, $CD11b^+Ly6c^+Ly6g^+$, $CD11b^+Ly6c^{++}Ly6g^-$, $CD11b^+Ly6c^{++}Ly6g^-$, $CD11b^+Lineage^-(CD3, CD14, CD19$ and $CD56)HLA-DR^-CD33^+$ or $CD11b^+CD14^+HLA-DR^-CD15^-$, more preferably phenotypes of $CD11b^+Gr1^{hi}$, $CD11b^+F480^-Gr1^+$, $CD11b^+Ly6c^{hi}$, $CD11b^+Ly6c^+Ly6g^+$ or $CD11b^+Ly6c^{++}Ly6g^-$ in mice, and $CD11b^+Ly6c^{++}Ly6g^-$, $CD11b^+Lineage^-(CD3, CD14, CD19$ and $CD56)HLA-DR^-CD33^+$ or $CD11b^+CD14^+HLA-DR^-CD15^-$ in human.

The anticancer agent may be at least one selected from the group consisting of a chemotherapeutic agent, a targeted therapeutic agent, an antibody therapeutic agent, an immunotherapeutic agent, and a hormone therapeutic agent, but is not limited thereto.

In the preferred embodiment of the present invention, it is verified that the decitabine suppresses creation of a cell population of myeloid-derived suppressor cells created in spleen and bone marrow in tumorigenic mice and induces apoptosis of the cell population of myeloid-derived suppressor cells, and thus the decitabine may be used as an anti-cancer supplement for anticancer immunotherapy.

Hereinafter, the present invention will be described in detail by Examples.

However, the following Examples just exemplify the present invention, and the contents of the present invention are not limited to the following Examples.

<Example 1> Preparation of Tumorigenic Mice

150 µl PBS including a colon cancer cell line MC38 $1.5 \times 10^6$ expressing a human CEA gene was injected hypodermically to the right flank of a 7 to 8-week-old female B6 mouse to form a tumor. The mouse was bred in a Seoul National University laboratory under a temperature of 23.5±1° C. and a humidity of 50±5% in a light/dark cycle of 12 hours. All animal experiments followed the guideline of the Animal Ethics Committee of Seoul National University.

<Example 2> Changes in Tumor Size and Survival Rate of Tumorigenic Mice According to Administration of Decitabine It was verified whether decitabine was usable as an anticancer chemotherapy through immune treatment based on a bone marrow-based specific drug effect. First, in order to verify an effect of the decitabine on the tumorigenic mice, the decitabine was administrated to the tumorigenic mice prepared in Example 1 and then changes in tumor size and survival rate were measured.

Particularly, in the tumorigenic mice prepared in Example 1, decitabine (DAC) at a concentration of 40 mg/ml purchased from Sigma Co., Ltd. was diluted with 100 µl PBS to be 0, 0.125, 0.25, 0.5, and 1 mg/kg per mouse and then administrated in the right abdominal cavity (every 2 days and a total of 10 times) for each concentration to verify the tumor size and the survival rate. The tumor size was calculated by the following Equation after measuring a width and a length of a tumor mass at an interval of 2 to 3 days from the time when 10 days elapsed after injecting tumor cells: Long length×short length×short length/2. In the survival rate, the number of surviving mice in each group was calculated by the following Equation: The number of surviving mice/a total number of mice×100

As a result, as shown in FIG. 1, it was confirmed that there was no difference of the tumor size itself or the survival rate according to a dose concentration of the decitabine. Accordingly, it is verified that a change in the number of immune cells by the decitabine administration may exclude a possibility to be an effect according to the tumor size and exclude a toxicity induction possibility by repeated administration.

<Example 3> Change in the Number of Cells in Spleen and Bone Marrow of Tumorigenic Mice According to Intraperitoneal Administration of Decitabine or Gemcitabine It was well-known that gemcitabine suppressed myeloid-derived suppressor cells (MDSC) derived from the tumor (Clin Cancer Res 2005; 11(18) Sep. 15, 2005), and the gemcitabine has been used as an anticancer chemotherapeutic agent. Accordingly, whether the decitabine is usable as an anticancer chemotherapeutic agent like the gemcitabine was verified through the comparison with the gemcitabine. First, in order to verify effects of decitabine and gemcitabine on cells in the spleen and the bone marrow, the decitabine and the gemcitabine were administrated to the tumorigenic mice prepared in Example 1 and then the number of cells in the spleen and the bone marrow was measured.

Particularly, in the tumorigenic mice prepared in Example 1, decitabine (DAC) or gemcitabine (GEM) were diluted with 100 µl PBS to be 0, 0.25, 0.5 mg/kg per mouse, administrated in the right abdominal cavity (every 2 days and a total of 10 times) for each concentration, and then sacrificed to extract the spleen and the bone marrow. Thereafter, spleen cells and bone marrow cells were extracted and stained by a trypan blue staining method and then the number of cells was measured by using a hematocytometer.

Figure 2:
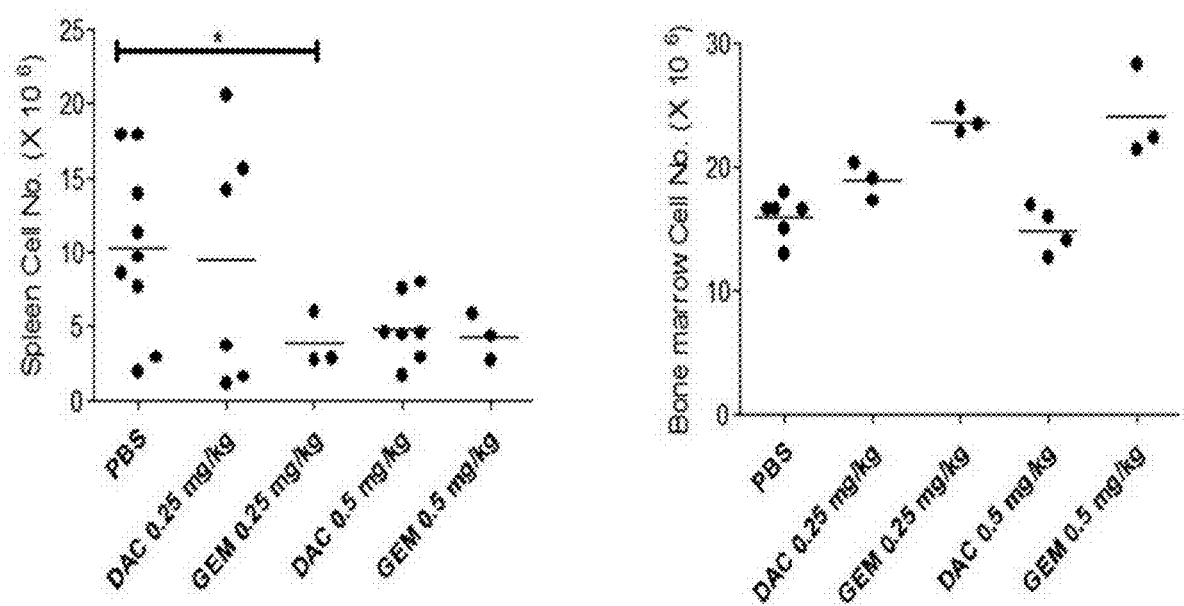
FIG. 2 is a diagram illustrating a change in the number of cells in spleen and bone marrow according to administration of decitabine (DAC) and gemcitabine (GEM) for each concentration (0, 0.25, 0.5 mg/kg) in tumorigenic mice.

As a result, as shown in FIG. 2, it was confirmed that when the dose concentration of the decitabine was 0.5 mg/kg, the number of spleen cells was significantly reduced (at a left of FIG. 2), whereas the number of bone marrow cells was not significantly exhibited (at a right of FIG. 2). In the case of administrating the gemcitabine, it was verified that the number of bone marrow cells was increased in a concentration-dependent manner (at a right of FIG. 2).

<Example 4> Change in the Number of Immune Cells in Spleen of Tumorigenic Mice According to Intraperitoneal Administration of Decitabine or Gemcitabine <Example 4-1> Change in the Number of Immune Cells in Spleen of Tumorigenic Mice According to Intraperitoneal Administration of Decitabine or Gemcitabine In order to verify effects of decitabine and gemcitabine on immune cells in the spleen, the decitabine and the gemcitabine were administrated to the tumorigenic mice prepared in Example 1 and then the numbers of cells in a T cell population, a B cell population, an NK cell population, an NKT cell population, and a myeloid-based cell population in the spleen were measured.

Particularly, by the method disclosed in Example 3, decitabine (DAC) or gemcitabine (GEM) was administrated and then the spleen was extracted. Thereafter, each immune cell population were stained with fluorescence-bound antibodies purchased by BD Corporation and then the number of cells was measured through a flow cytometer.

Figure 3:
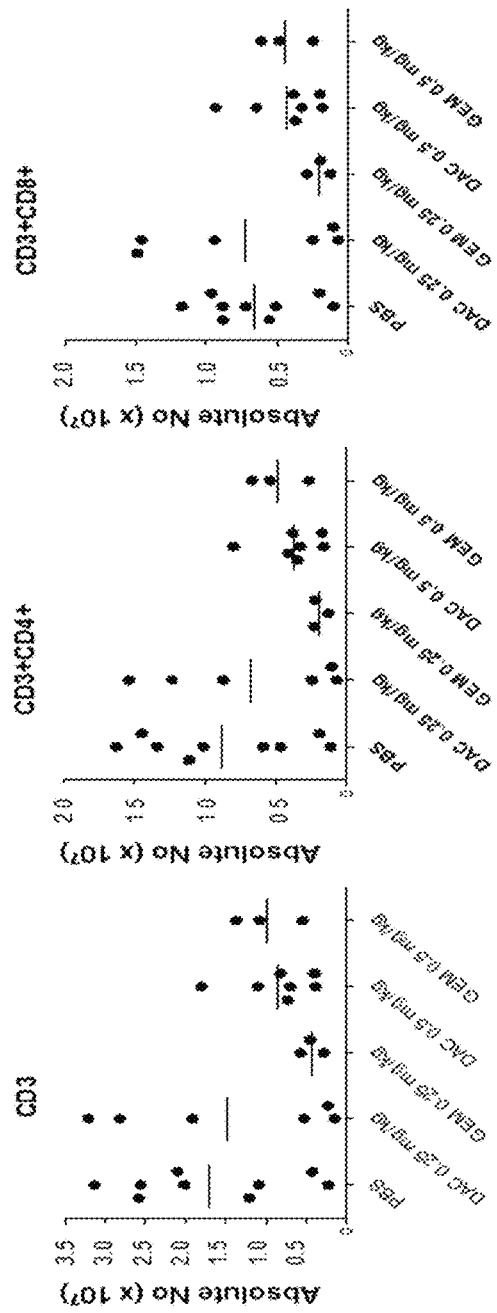
FIG. 3 is a diagram illustrating a change in the number of cells of T cell populations ($CD3^+$, $CD3^+CD4^+$, $Cd3^+CD8^+$) in spleen according to administration of DAC and GEM for each concentration in tumorigenic mice.
Figure 3:
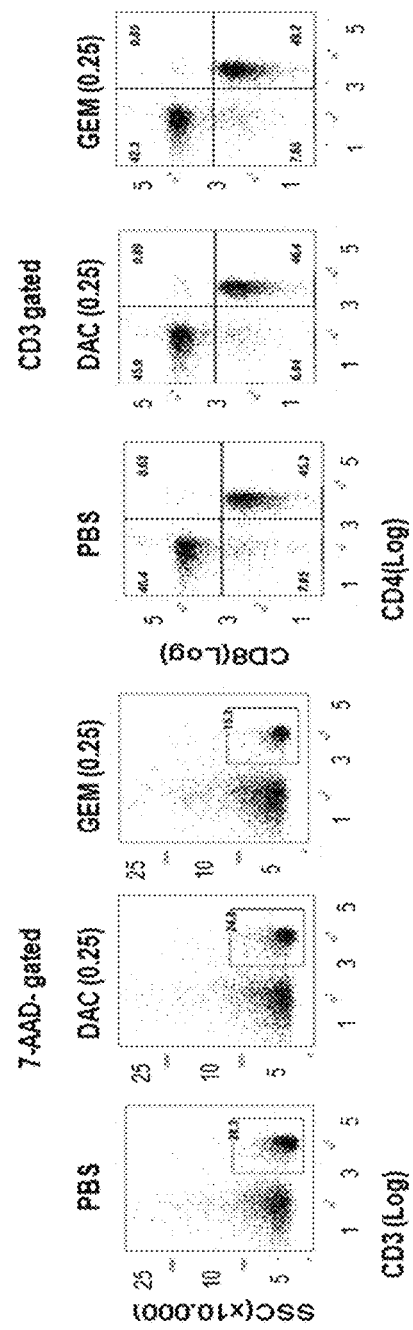

In order to measure the number of cells in the T cell population, an anti-CD3 antibody, an anti-CD4 antibody, and an anti-CD8 antibody were used (FIG. 3).

In order to the number of cells in the B cell population, an anti-B220 antibody was used. Further, in order to measure the number of cells in the NK and NKT cell populations, anti-CD3 and anti-NK1.1 antibodies were used (FIG. 4).

Figure 5:
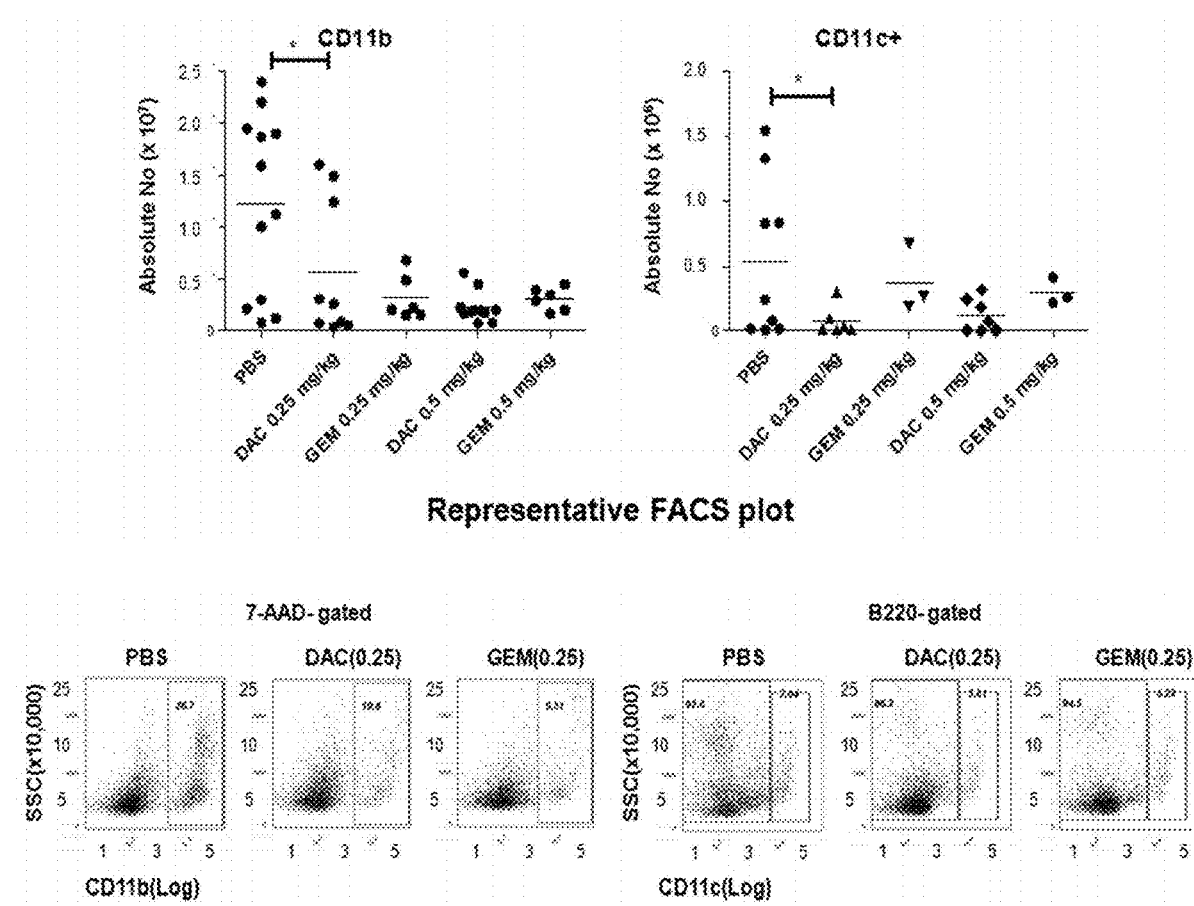
FIG. 5 is a diagram illustrating a change in the number of cells of a myeloid lineage cell ($CD11b^+$ or $CD11c^+$) population in spleen according to administration of DAC and GEM for each concentration in tumorigenic mice.

In order to measure the number of cells in the myeloid-based cell population, an anti-CD11b antibody and an anti-CD11c antibody were used (FIG. 5).

As a result, as shown in FIG. 3, it was confirmed that the gemcitabine caused a rapid reduction of T cell populations $CD3^+$, $CD3^+CD4^+$, and $CD3^+CD8^+$ in the spleen from a low concentration, whereas in the decitabine, a reduction rate of the T cell populations was slight as compared with the gemcitabine. Since the $CD3^+$ T cell population is an important cell population to kill the tumor cells, the reduction of the $CD3^+$ T cells caused by the gemcitabine at a low concentration may cause a result that the growth of the tumor is not suppressed.

Figure 4:
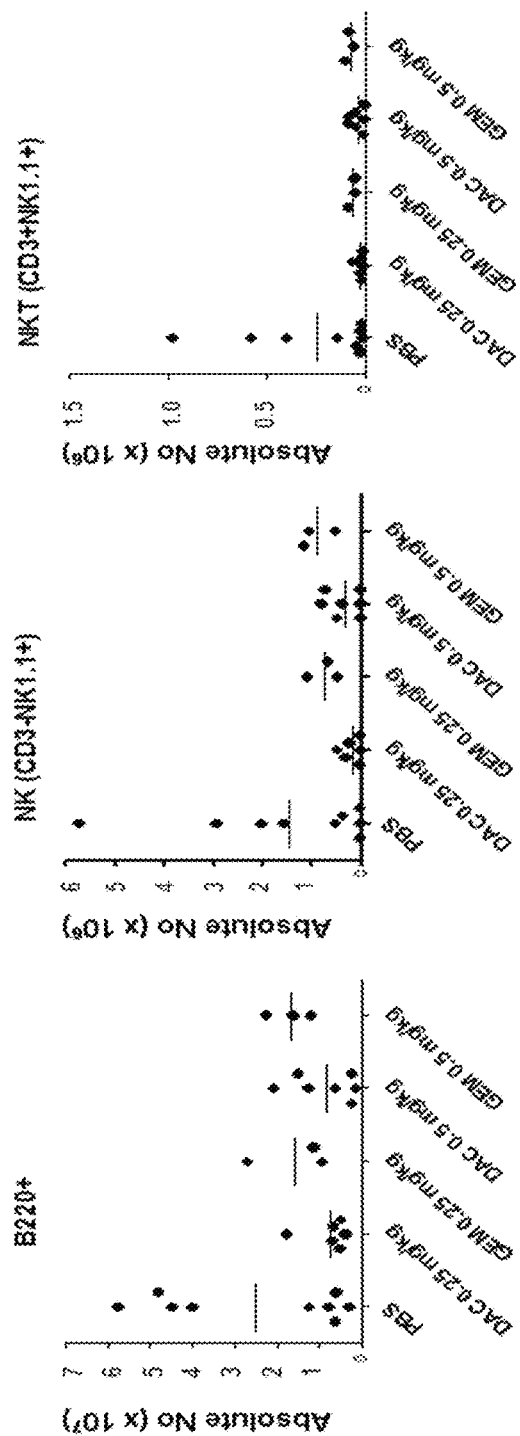
FIG. 4 is a diagram illustrating a change in the number of cells of B ($B220^+$), NK ($CD3^-$ $NK1.1^+$), NKT ($CD3^+$ $NK1.1^+$) groups in spleen according to administration of DAC and GEM for each concentration in tumorigenic mice.
Figure 4:
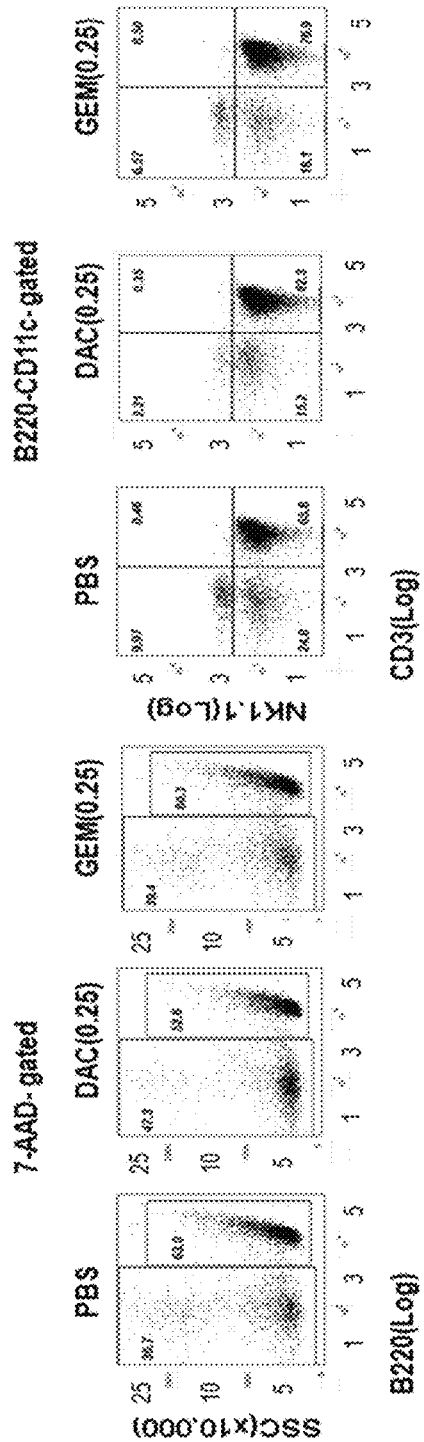

Further, as illustrated in FIG. 4, it was verified that at a lower concentration of the decitabine than the gemcitabine, the reduction of the B cell population $B220^+$ and the NK cell population $CD3^-NK1.1^+$ in the spleen was induced and the significant change in the NKT cell population $CD3^+NK1.1^+$ was not induced. The reduction of the B cell population and the NK cell population caused by the decitabine may cause an effect of relatively reinforcing the number and the activity of T cell population.

Further, as shown in FIG. 5, it was confirmed that the decitabine induced the rapid reduction of the myeloid-based cell populations $CD11b^+$ and $CD11c^+$ in the spleen as compared with the gemcitabine. The tumor cells produce various myeloid-based cell populations for helping in the growth of the tumor cells in vivo and thus the reduction of the myeloid-based cell populations may expect an effect of neutralizing factors for helping in the growth of the tumor cells.

<Example 4-2> Change in the Number of Cells of Subpopulation of Myeloid-Based Cell Population in Spleen of Tumorigenic Mice According to Intraperitoneal Administration of Decitabine or Gemcitabine In order to verify an effect of decitabine or gemcitabine on cells of a subpopulation of myeloid-based cell populations in the spleen and the bone marrow, decitabine and gemcitabine were administrated to the tumorigenic mice prepared in Example 1 and then the numbers of cells in a granulocytic cell population, a monokaryotic cell population, and an MDSC cell population were measured.

Particularly, by the method disclosed in Example 3, decitabine (DAC) or gemcitabine (GEM) was administrated and then the spleen was extracted. Thereafter, monokaryotic and granulocytic cell populations were stained with fluorescence-bound antibodies purchased by BD Corporation and then the numbers of cells were measured through a flow cytometer.

Figure 6:
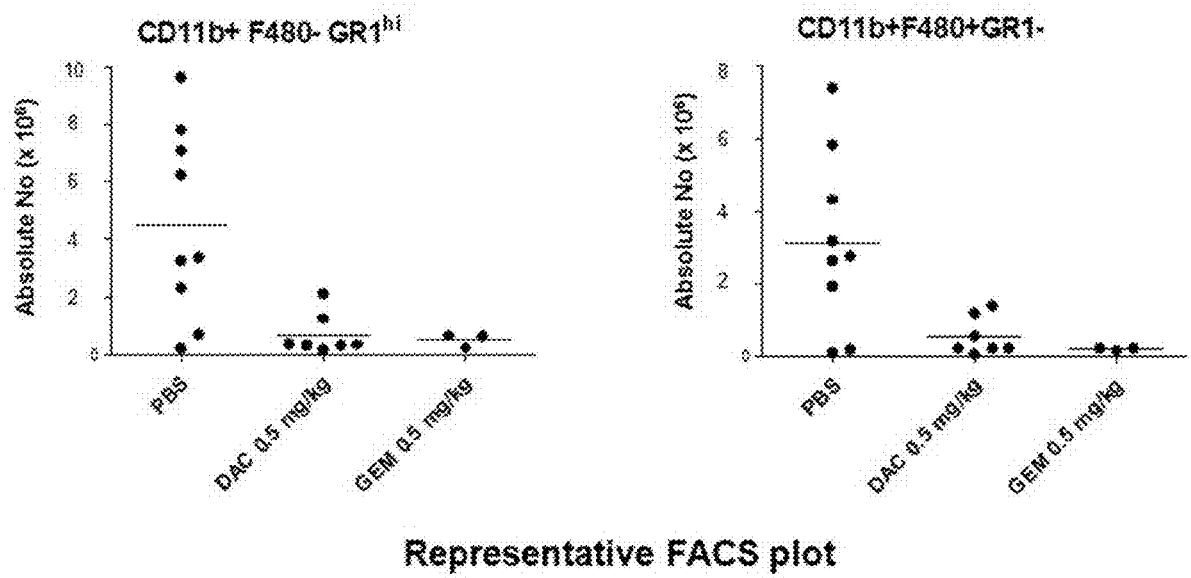
FIG. 6 is a diagram illustrating changes in the number of cells of a granulocytic cell population ($CD11b^+F480^-Gr1^{hi}$) and a monokaryotic cell population ($CD11b^+F480^+Gr1^-$) in spleen according to administration of DAC and GEM for each concentration in tumorigenic mice.
Figure 6:
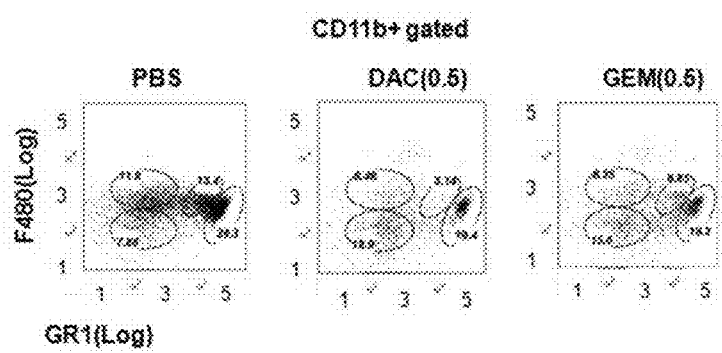

In order to measure the numbers of cell in the monokaryotic cell population and the granulocytic cell population, anti-CD11b, anti-F480 and anti-Gr1 antibodies were used (FIG. 6).

Figure 7:
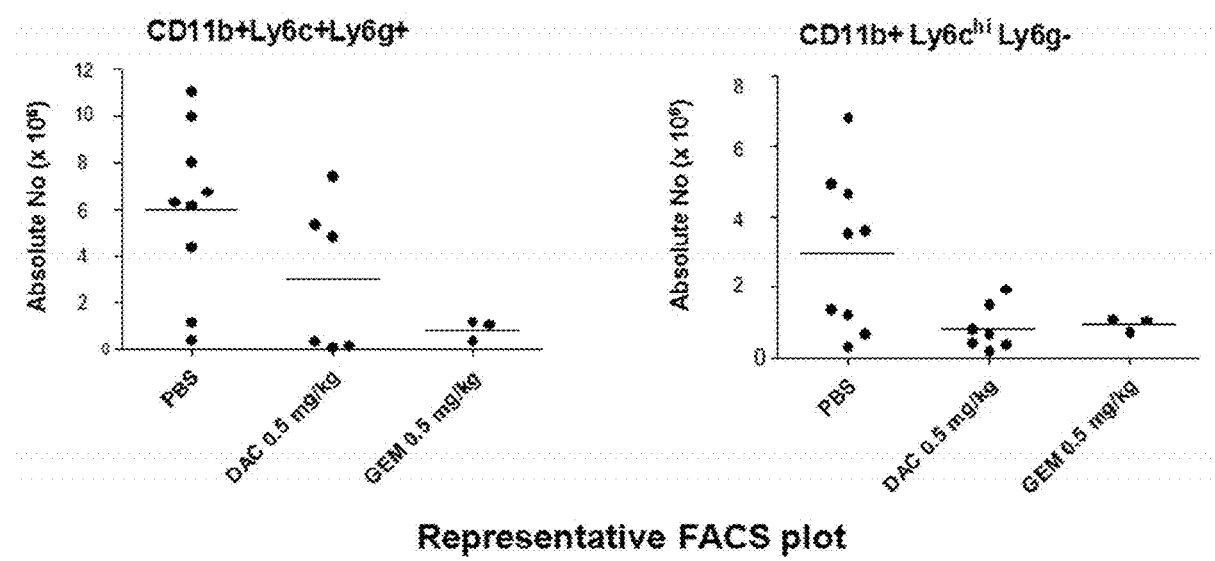
FIG. 7 is a diagram illustrating changes in the number of cells of two subpopulations ($CD11b^+Ly6c^+Ly6g^+$ or $CD11b^+Ly6c^{hi}Ly6g^-$) of a cell population ($CD11b+Gr1^{hi}$) of myeloid-derived suppressor cells (MDSC) in spleen according to administration of DAC and GEM for each concentration in tumorigenic mice.
Figure 7:
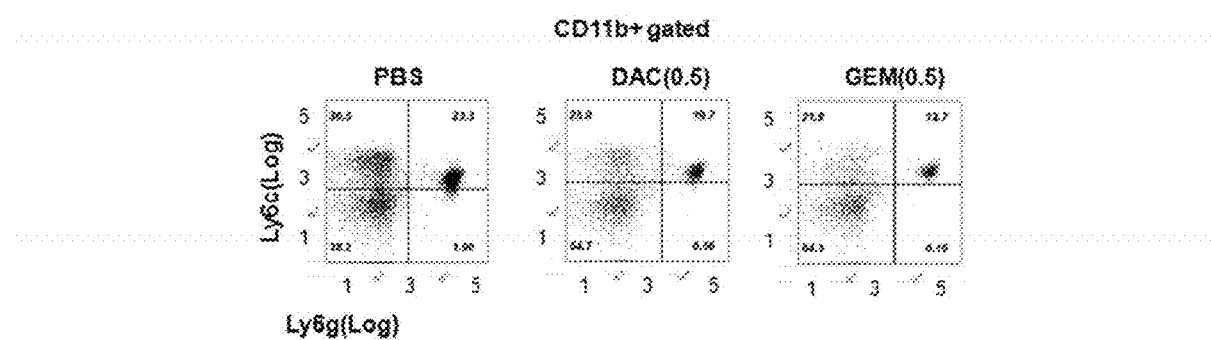

In order to measure the number of cells of the subpopulation of the MDSC cell population, anti-CD11b, anti-Ly6c and anti-Ly6g antibodies were used (FIG. 7).

As a result, as shown in FIG. 6, the decitabine induced a rapid reduction in a granulocytic cell population $CD11b^+F480^-Gr1^{hi}$ and a monokaryotic cell population $CD11b^+F480^+Gr1^-$ in the spleen, similarly to the gemcitabine.

Further, as shown in FIG. 7, the decitabine induced a rapid reduction in subpopulations $CD11b^+Ly6c^+Ly6g^+$, $CD11b^+Ly6c^{hi}$ of the MDSC cell population in the spleen, to the degree of similar to or higher than the gemcitabine.

Accordingly, through the result of Example 4, it was verified that the decitabine induced a rapid reduction of the MDSC cell population in the spleen which was more excellent than the gemcitabine.

<Example 5> Change in the Number of Immune Cells in Bone Marrow of Tumorigenic Mice According to Intraperitoneal Administration of Decitabine or Gemcitabine <Example 5-1> Change in the Number of Immune Cells in Bone Marrow of Tumorigenic Mice According to Intraperitoneal Administration of Decitabine or Gemcitabine In order to verify effects of decitabine and gemcitabine on immune cells in the bone marrow, the decitabine and the gemcitabine were administrated to the tumorigenic mice prepared in Example 1 and then the numbers of cells in a T cell population, a B cell population, an NK cell population, an NKT cell population, and a myeloid-based cell population in the bone marrow were measured.

Particularly, by the method disclosed in Example 3, decitabine (DAC) or gemcitabine (GEM) was administrated and then the bone marrow was extracted. Thereafter, the bone marrow was stained by using the antibodies disclosed in Example 4-1, and then the number of cells was measured through a flow cytometer (FIGS. 8 to 10).

Figure 8:
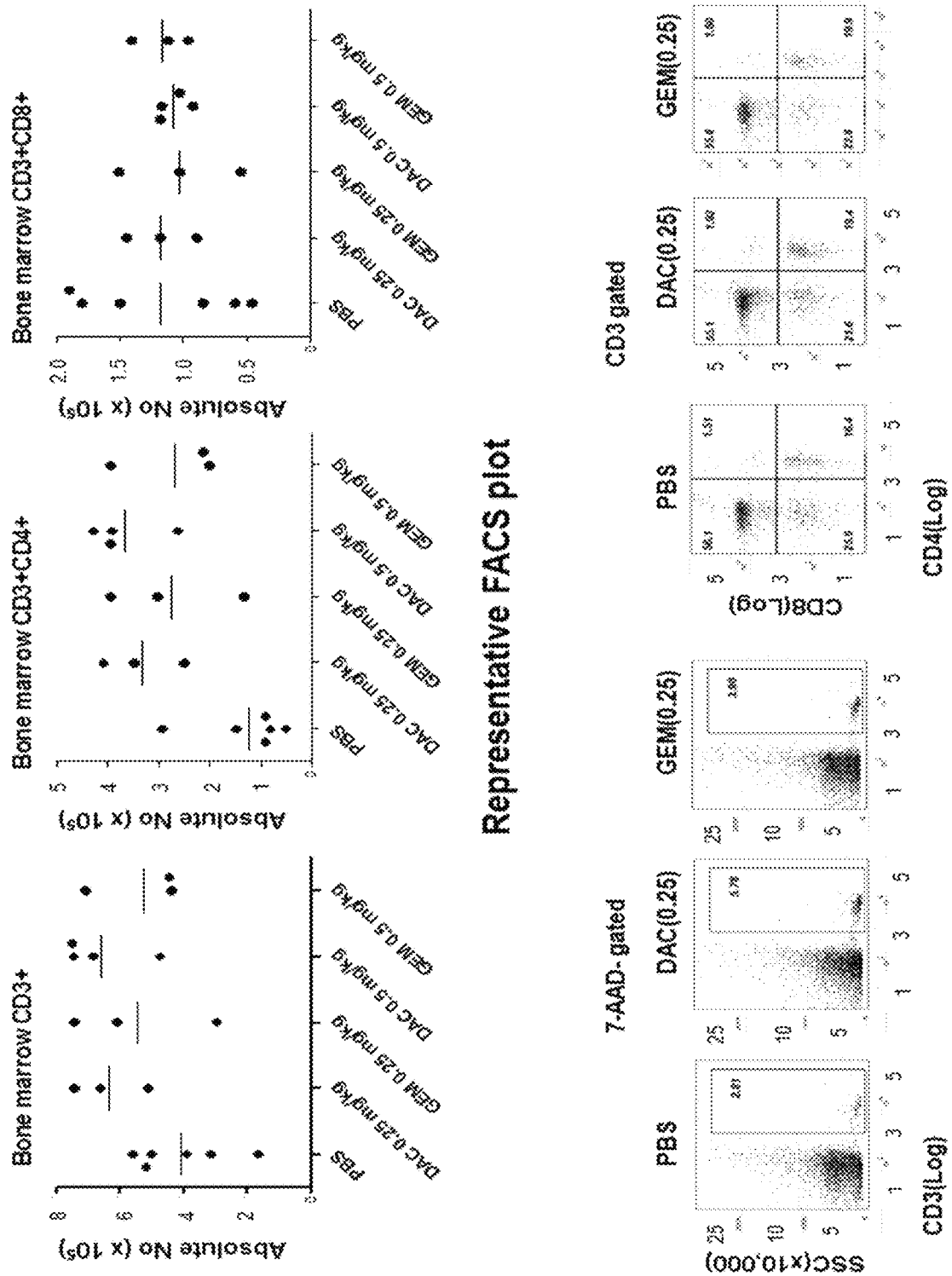
FIG. 8 is a diagram illustrating a change in the number of cells of T cell populations ($CD3^+$, $CD3^+CD4^+$, $CD3^+CD8^+$) in bone marrow according to administration of DAC and GEM for each concentration in tumorigenic mice.

As a result, as shown in FIG. 8, it was confirmed that the number of some T cell populations $CD3^+$ and $CD3^+CD4^+$ in the bone marrow was increased by the gemcitabine and the decitabine. The T cell populations are cell populations of directly killing the tumor cells and thus the increase in the number of T cell populations caused by the drug may increase the tumor cell killing effect.

Figure 9:
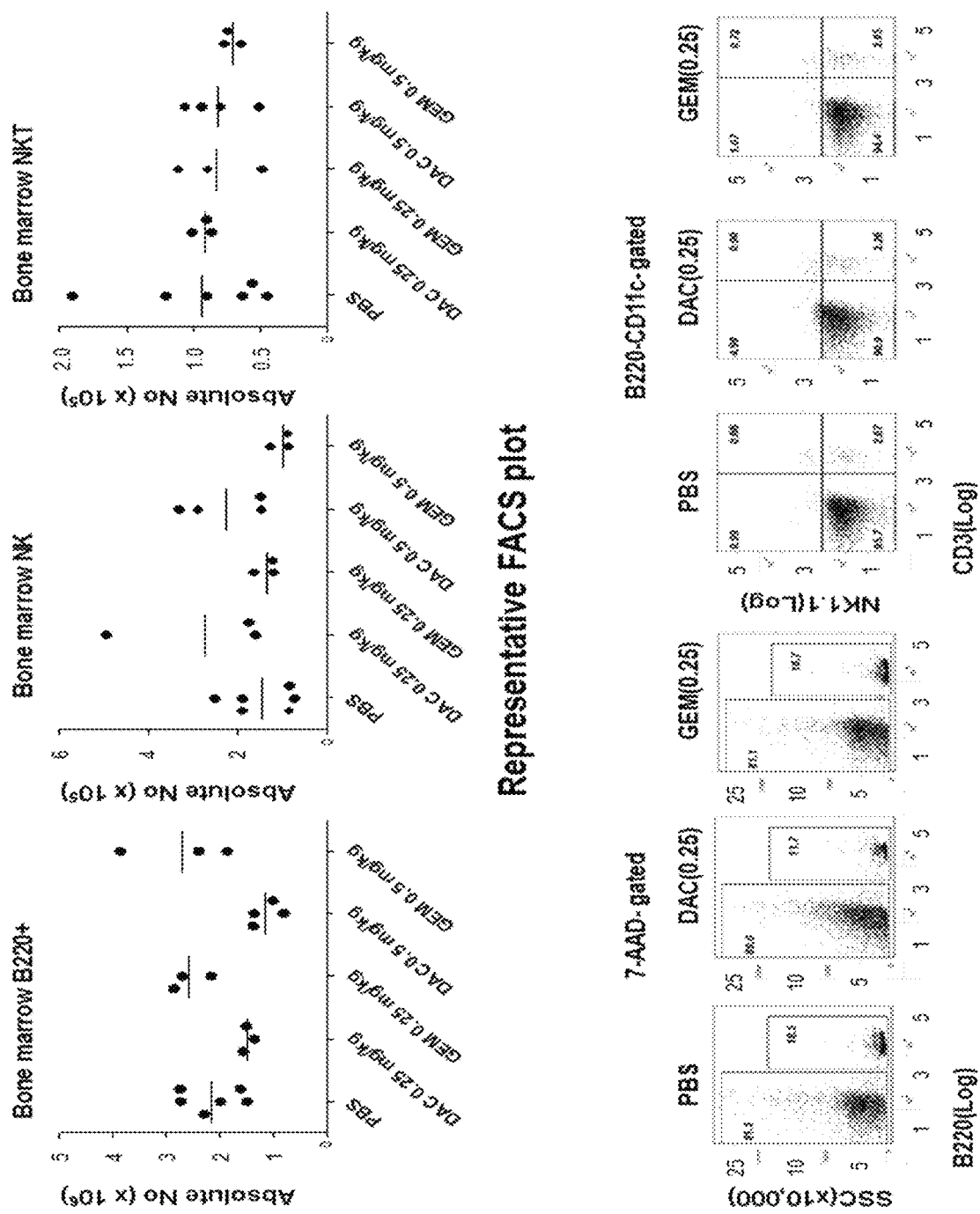
FIG. 9 is a diagram illustrating changes in the number of cells of B ($B220^+$), NK ($CD3^-$ $NK1.1^+$), NKT ($CD3^+$ $NK1.1^+$) groups in bone marrow according to administration of DAC and GEM for each concentration in tumorigenic mice.

Further, as shown in FIG. 9, it was confirmed that as compared with the gemcitabine, the decitabine induced the reduction of the B cell population $B220^+$ in the bone marrow and the significant changes in the NK cell population $CD3^-NK1.1^+$ and the NKT cell population $CD3^+NK1.1^+$ were not induced. The reduction of the B cell population caused by the decitabine may cause an effect of relatively reinforcing the number and the activity of T cell population.

Figure 10:
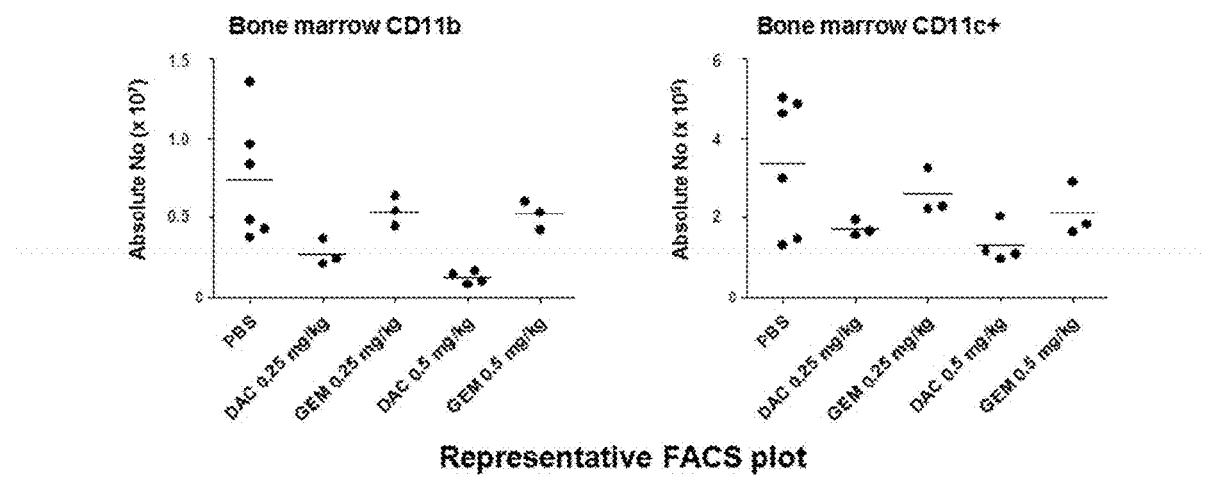
FIG. 10 is a diagram illustrating a change in the number of cells of—myeloid lineage cell populations ($CD11b^+$ or $CD11c^+$) in bone marrow according to administration of DAC and GEM for each concentration in tumorigenic mice.
Figure 10:
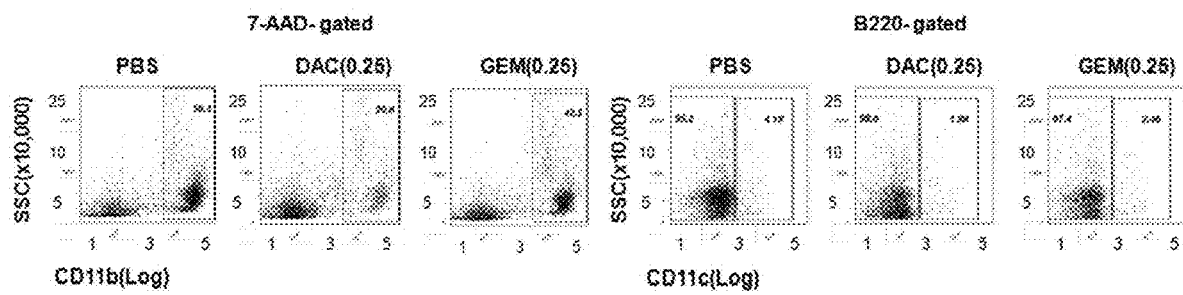

Further, as shown in FIG. 10, it was confirmed that the decitabine induced the rapid reduction of the myeloid-based cell populations $CD11b^+$ and $CD11c^+$ in the bone marrow as compared with the gemcitabine. The reduction of the myeloid-based cell population may expect an effect of neutralizing factors for helping in the growth of the tumor cells.

<Example 5-2> Change in the Number of Cells of Subpopulation of Myeloid-Based Cell Population in Bone Marrow of Tumorigenic Mice According to Intraperitoneal Administration of Decitabine or Gemcitabine In order to verify an effect of decitabine or gemcitabine on cells of a subpopulation of myeloid-based cell populations in the bone marrow, decitabine and gemcitabine were administrated to the tumorigenic mice prepared in Example 1 and then the numbers of cells in a granulocytic cell population, a monokaryotic cell population, and an MDSC cell population in the bone marrow were measured.

Particularly, by the method disclosed in Example 3, decitabine (DAC) or gemcitabine (GEM) was administered and then the bone marrow was extracted. Thereafter, the bone marrow was stained by using the antibodies disclosed in Example 4-2, and then the number of cells was measured through a flow cytometer (FIGS. 11 to 12).

Figure 11:
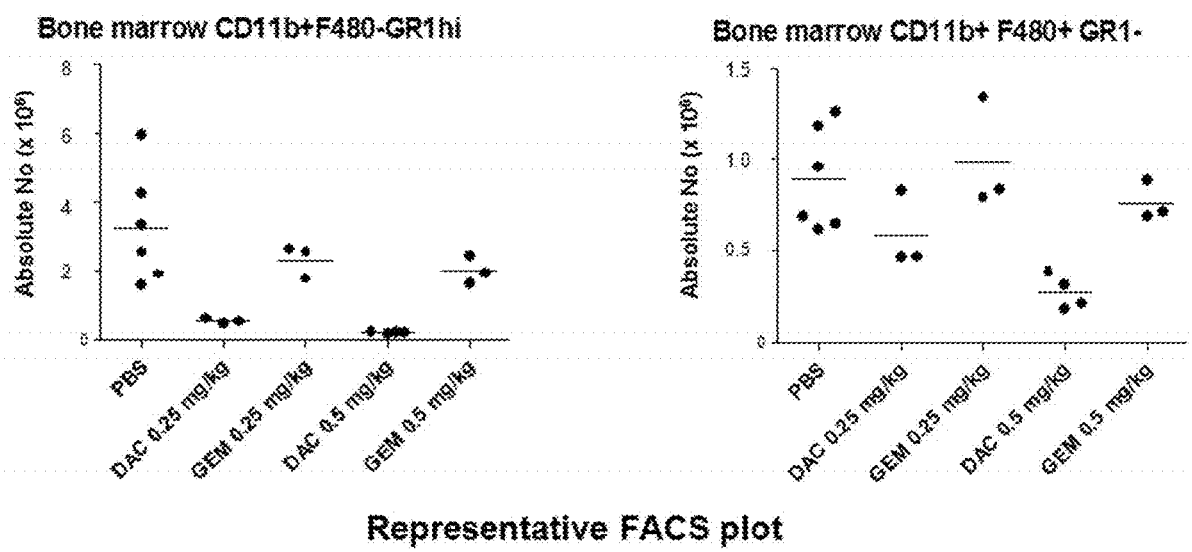
FIG. 11 is a diagram illustrating changes in the number of cells of a granulocytic cell population ($CD11b^+F480^-Gr1^{hi}$) and a monokaryotic cell population ($CD11b^+F480^+Gr1^-$) in bone marrow according to administration of DAC and GEM for each concentration in tumorigenic mice.
Figure 11:
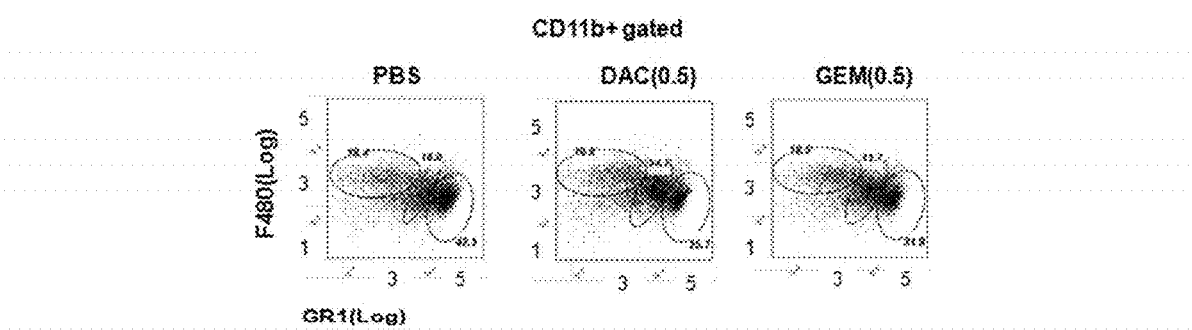

As a result, as shown in FIG. 11, it was confirmed that the decitabine induced a more rapid reduction of a granulocytic cell population $CD11b^+F480^-Gr1^{hi}$ and a monokaryotic cell population $CD11b^+F480^+Gr1^-$ than the gemcitabine and thus the decitabine suppressed an increase in various myeloid-based cell populations for helping in the growth of the tumor cells created by the tumor cells.

Figure 12:
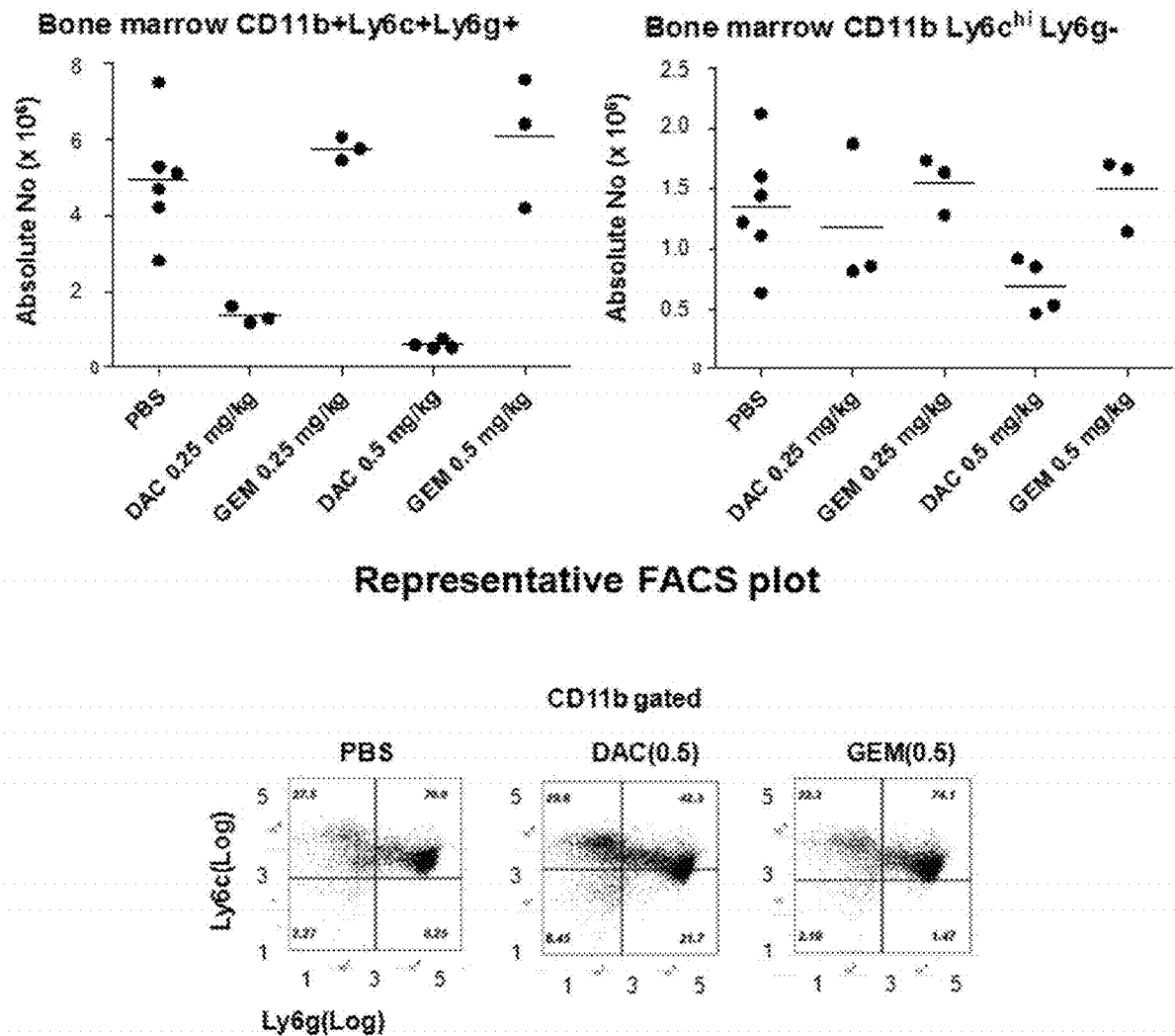
FIG. 12 is a diagram illustrating changes in the number of cells of two subpopulations ($CD11b^+Ly6c^+Ly6g^+$ or $CD11b^+Ly6c^{hi}Ly6g^-$) of a cell population ($CD11b^+Gr1^{hi}$) of myeloid-derived suppressor cells (MDSC) in bone marrow according to administration of DAC and GEM for each concentration in tumorigenic mice.

Further, as shown in FIG. 12, it was confirmed that the decitabine induced a rapid reduction of subpopulations $CD11b^+Ly6c^+Ly6g^+$, and $CD11b^+Ly6c^{hi}$ of the MDSC cell population in the bone marrow to a much higher degree than the gemcitabine, and thus the decitabine reduced the MDSC cell population to a significantly better degree than the gemcitabine having the pre-verified efficacy.

Accordingly, through the result of Example 5, it was verified that the decitabine induced a rapid reduction of the MDSC cell population in the bone marrow which was more excellent than the gemcitabine.

<Example 6> Induction of Apoptosis of MDSC Cell Population in Tumorigenic Mice Caused by Treatment of Decitabine or Gemcitabine In Vitro In order to verify effects of decitabine and gemcitabine on apoptosis of an MDSC cell population, the decitabine or the gemcitabine was treated in vitro and then a change in the number of cells in the MDSC cell population was measured.

Particularly, from the tumorigenic mice prepared in Example 1, the bone marrow was extracted and then bone marrow stem cells were isolated. Thereafter, while the bone marrow stem cells in a bottom well and cells of a colon cancer cell line MC38 expressing a CEA gene were co-cultured in an insert well for a total of 3 days with a DMEM culture medium by using a Transwell system, the decitabine and the gemcitabine of concentrations of 50 nM were treated at a third day after cell culture, respectively, and then cells after two days were collected. Thereafter, in order to measure the numbers of cells in the myeloid-based cell population and the MDSC cell population, the cell populations were stained by using an anti-CD11b antibody and an anti-GR1 antibody and then the number of cells was measured through a flow cytometer.

Figure 13:
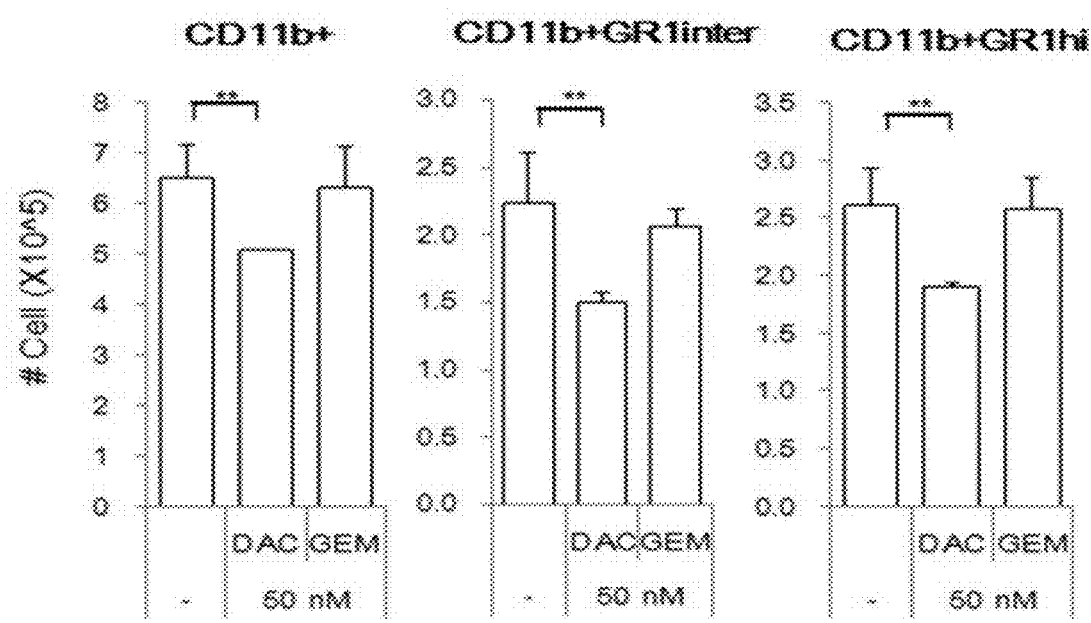
FIG. 13 is a diagram illustrating a change in the number of cells of $CD11b^+$ myeloid cells and myeloid-derived MDSC cell populations ($CD11b^+GR1^{inter}$ or $CD11b^+GR1^{hi}$) induced by tumor cells in vitro according to administration of DAC and GEM.

As a result, as shown in FIG. 13, it was confirmed that as compared with the gemcitabine, the decitabine induced the rapid reduction of the number of cells in the MDSC cell population and thus the decitabine induced apoptosis of the MDSD cell population which was better than the gemcitabine.

<Example 7> Molecular Change in Tumor Cell Itself Caused by Decitabine

In order to verify a possibility of a result that the MDSC creation itself in the bone marrow is decreased by the tumor cells, in addition to a direct apoptotic effect of the MDSC by the reduction of the MDSC cell population caused by the decitabine, an expression change in cytokines inducing the creation of the MDSC cell population after treating the decitabine in the tumor cells was measured.

Particularly, the decitabine was treated in each well for each concentration 0, 10, 100 nM in a colon cancer cell line MC38 expressing the CEA gene which was cultured for 1 week in a 6-well plate and cultured for 48 hours, and then the cells were collected. Thereafter, from the collected cells, total RNA was isolated by using a trizol reagent (Invitrogen, Carlsbad, Calif.) and then the isolated RNA 5 μg reacted with reverse transcriptase for 1 hour at 42° C. to synthesize a cDNA and 5 minutes at 95° C. to inactivate the enzyme. Polymerase chain reaction (PCR) was performed by using a primer in the following Table 1 by using the cDNA as a template of PCR and a PCR product was electrophoresed with an agarose gel and visualized to confirm expression of IL-6, IFN-γ and VEGF genes.

TABLE 1

| Primer | Sequence (5'→3') | |
|---|---|---|
| IL-6 | Forward | TGGAGTCACAGAAGGAGTGGCTAAG (SEQ ID NO: 1) |
| | Reverse | TCTGACCACAGTGAGGAATGTCCAC (SEQ ID NO: 2) |
| IFN-γ | Forward | AGGTCAACAACCCACAGGTCCA (SEQ ID NO: 3) |
| | Reverse | CCAGATACAACCCCGCAATCAC (SEQ ID NO: 4) |
| VEGF | Forward | CTGTGCAGGCTGCTGTAACG (SEQ ID NO: 5) |
| | Reverse | GTTCCCGAAACCCTGAGGAG (SEQ ID NO: 6) |

Figure 14:
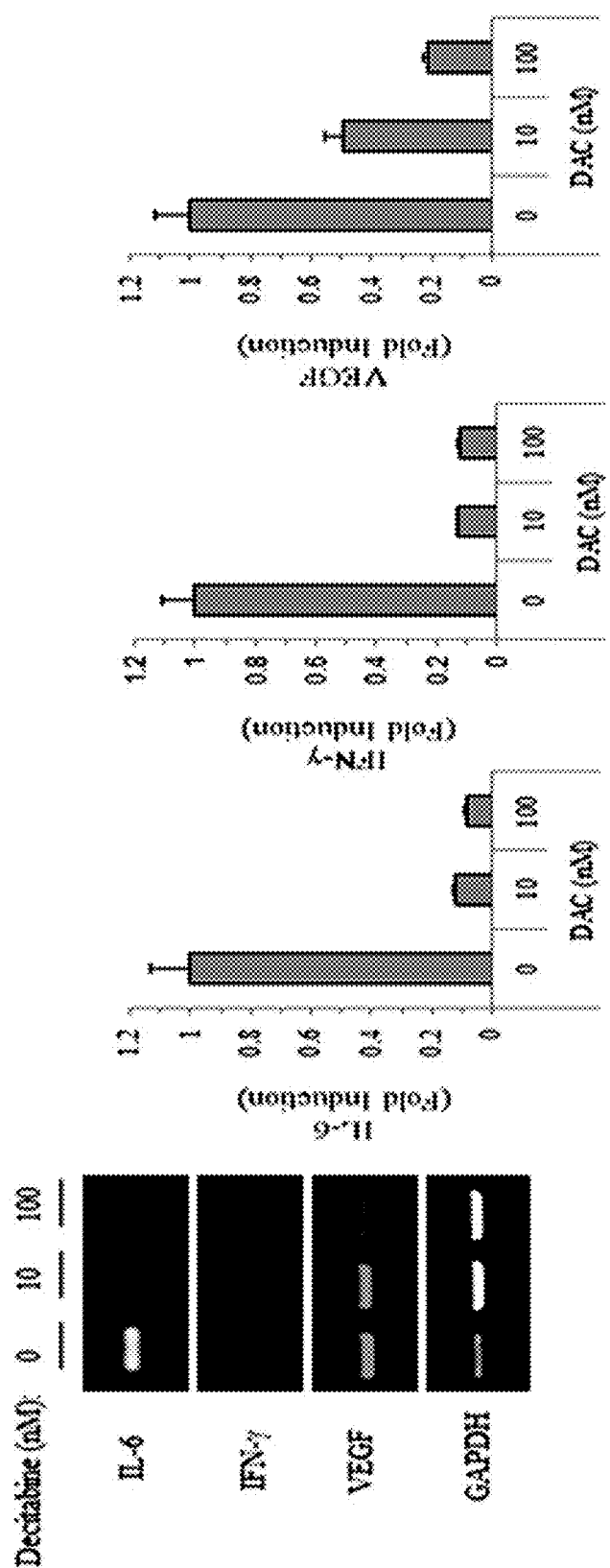
FIG. 14 is a diagram illustrating a change in expression level of cytokine produced from tumor after in vitro treatment of DAC in tumor cells.

As a result, as shown in FIG. 14, it was verified that the creation degree of IL-6, IFN-γ and VEGF was reduced in the tumor by the decitabine and thus the decitabine may induce reduction to the degree of the MDSC creation in the bone marrow caused by the tumor even in addition to direct apoptosis of the MDSC.

<Example 8> Cancer Immunotherapy Effects Using Decitabine

In order to verify whether the reduction of the MDSC cell population caused by the decitabine may enhance an effect of a cancer immunotherapy in the related art, a combination therapy with dendritic cell vaccine was performed.

Particularly, dendritic cell vaccine ($1 \times 10^6$ cells) having a tumor antigen hOlmf4 were at 10-th, 14-th, 18-th days into mice with melanoma expressing the tumor antigen hOlmf4 after tumor-injection. From 22 days after the tumor injection, the decitabine (DAC) was diluted with 100 μl PBS to be 0 and 1 mg/kg per mouse and then administrated into the tail vein (every 2 days, a total of 5 times) of the mice and then the tumor size was measured. The tumor size was calculated by the following Equation after measuring a width and a length of a tumor mass at an interval of 2 to 3 days from the time when 10 days elapsed after injecting tumor cells: Long length×short length×short length/2.

Figure 15:
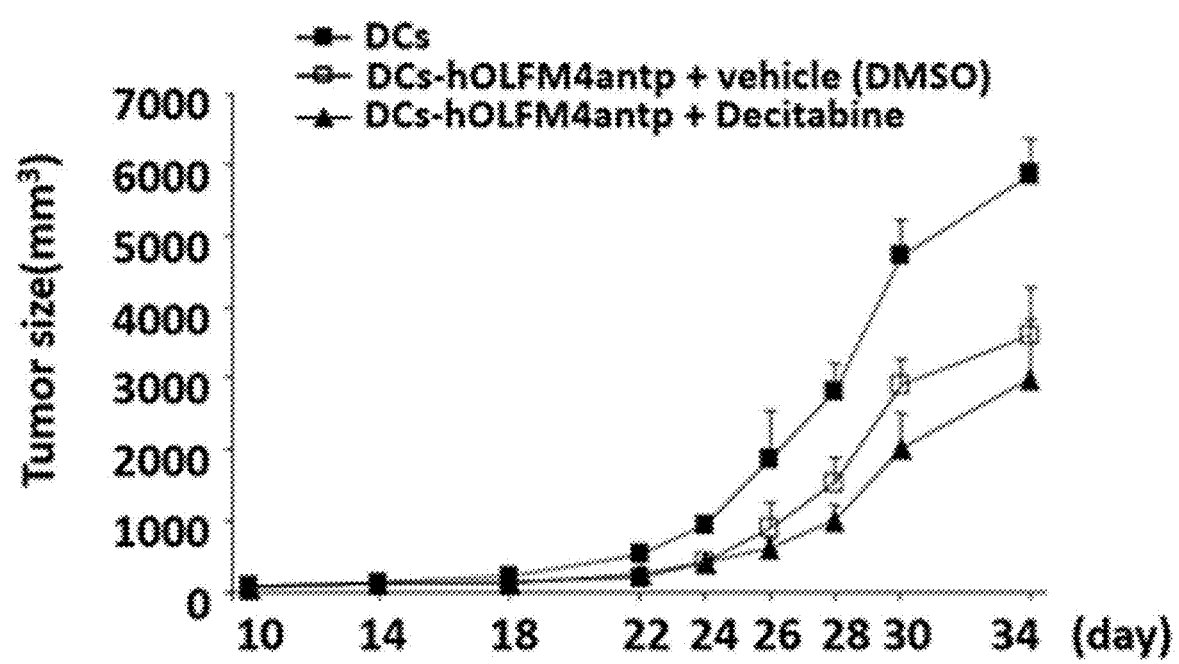
FIG. 15 is a diagram illustrating a change in tumor size after treating both dendritic cell vaccine in combination with DAC.

As a result, as shown in FIG. 15, it was confirmed that in a group of administrating dendritic cell vaccine DC-hOlfm4antp, the growth of the tumor size was significantly delayed as compared with a group of treating dendritic cell DCs alone. Further, it was confirmed that in the case of simultaneously administrating the dendritic cell vaccine and the decitabine, the growth of the tumor was significantly reduced as compared with a single treatment group.

Accordingly, through Examples 1 to 8, it was verified that the decitabine had excellent effects of suppressing the MDSC and inducing the apoptosis as compared with the gemcitabine and may enhance the effect of a cancer immunotherapy. Further, when the decitabine has an excellent MDSC suppression effect at 0.5 mg/kg and a fifth part to a tenth part of an effective dose (5.25 mg/kg/once, 34 mg/kg/cycle) applied to an actual patient is compared with an effective dose of 120 mg/kg at which the gemcitabine has the MDSC suppression effect, it was verified that the effective dose is a low concentration of a hundredth part or more. Accordingly, it is verified that in order to enhance the anticancer immunotherapy efficiency, the decitabine can be used as a chemoadjuvant for the purpose of suppressing the MDSC and can be applied at a significantly low concentration as compared with the gemcitabine.

While the present invention has been described with respect to the specific embodiments, it will be apparent to those skilled in the art that various changes and modifications may be made without departing from the spirit and scope of the invention as defined in the following claims.

What is claimed is:

1. A method for reducing myeloid-derived suppressor cells in a spleen and bone marrow, comprising administering an effective amount of a pharmaceutical composition containing decitabine or its pharmaceutically acceptable salt to a subject having a colon cancer, wherein the decitabine or its pharmaceutically acceptable salt does not remove CD3 T lymphocytes in the spleen and the bone marrow, wherein the decitabine or its pharmaceutically acceptable salt is administered at a dose of 0.25 to 0.5 mg/kg.

2. The method according to claim 1, wherein the myeloid-derived suppressor cells of the subject having the colon cancer are at least one selected from the group consisting of phenotypes of $CD11b^+Gr1^{hi}$, $CD11b^+F480^-Gr1^+$, $CD11b^+Ly6c^{hi}$, $CD11b^+Ly6c^+Ly6g^+$, $CD11b^+Ly6c^{++}Ly6g^-$, $CD11b^+Lineage^-(CD3, CD14, CD19$ and $CD56)HLA-DR^-CD33^+$ and $CD11b^+CD14^+HLA-DR^-CD15^-$.

3. The method according to claim 1, wherein the decitabine or its pharmaceutically acceptable salt suppresses expression of cytokines inducing creation of the myeloid-derived suppressor cells in a cancer site.

4. The method according to claim 3, wherein the cytokine is at least one selected from a group of IL-6, IFN-g and VEGF.

5. The method according to claim 1, wherein the subject is a patient and a human equivalent dose (HED) of the decitabine or its pharmaceutically acceptable salt is administered.

6. The method according to claim 5, wherein the HED, calculated from 0.25 to 0.5 mg/kg, is 0.75 to 1.5 mg/m$^2$.

* * * * *